(12) United States Patent  
Tarn et al.

(10) Patent No.: US 9,155,823 B2  
(45) Date of Patent: Oct. 13, 2015

(54) DETERMINING DIALYSIS TREATMENT EFFECTIVENESS

(75) Inventors: Jeffrey Tarn, Walnut Creek, CA (US); Fei Wang, Concord, CA (US); Aiyuan Wang, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 13/214,519

(22) Filed: Aug. 22, 2011

(65) Prior Publication Data

US 2013/0053651 A1  Feb. 28, 2013

(51) Int. Cl.
*A61M 1/16* (2006.01)
*B01D 61/30* (2006.01)
*B01D 61/32* (2006.01)
*A61M 1/28* (2006.01)

(52) U.S. Cl.
CPC ............... *A61M 1/16* (2013.01); *A61M 1/1601* (2014.02); *A61M 1/1611* (2014.02); *A61M 1/28* (2013.01); *B01D 61/30* (2013.01); *B01D 61/32* (2013.01); *A61M 1/1603* (2014.02); *A61M 2205/50* (2013.01); *A61M 2205/502* (2013.01); *A61M 2205/52* (2013.01)

(58) Field of Classification Search
CPC ....... A61M 1/16; A61M 1/28; A61M 1/1611; A61M 1/1601; A61M 1/1603; A61M 2205/50; A61M 2205/52; A61M 2205/502; A61M 2205/505; B01D 61/243; B01D 61/28; B01D 61/30; B01D 61/32
USPC ..................... 210/85, 86, 94, 96.2, 138, 143, 210/645–647, 739; 604/4.01, 5.01, 6.01, 604/6.09, 29, 65–67; 600/301
See application file for complete search history.

(56) References Cited

U.S. PATENT DOCUMENTS

| 5,518,623 | A | * | 5/1996 | Keshaviah et al. ............ 210/646 |
| 5,645,734 | A | * | 7/1997 | Kenley et al. ................. 210/805 |
| 6,117,100 | A | * | 9/2000 | Powers et al. ................ 604/6.11 |
| 2003/0216677 | A1 | | 11/2003 | Pan et al. |
| 2006/0157413 | A1 | * | 7/2006 | Bene et al. ..................... 210/646 |
| 2007/0138069 | A1 | * | 6/2007 | Roncadi et al. .............. 210/96.2 |

(Continued)

FOREIGN PATENT DOCUMENTS

| DE | 102006032926 A1 | 1/2008 |
| EP | 1698360 A1 | 9/2006 |
| EP | 2005982 A1 | 12/2008 |
| WO | WO2008009380 A1 | 1/2008 |
| WO | WO 2010028860 A1 * | 3/2010 ............. A61M 1/16 |

(Continued)

OTHER PUBLICATIONS

International Search Report from corresponding PCT Application No. PCT/US2012/044318, mailed Oct. 2, 2012, 2 pages.

*Primary Examiner* — Joseph Drodge
(74) *Attorney, Agent, or Firm* — Fish & Richardson P.C.

(57) ABSTRACT

A method performed on a dialysis machine includes receiving a first value that represents a pre-dialysis body weight of a patient and receiving a second value that represents a volume of liquid (V) inside a body of the patient. The method also includes administering dialysis to the patient, calculating an instantaneous body weight (W) of the patient based at least in part on the first value, determining a length of time (t) for which the dialysis was administered to the patient, determining a dialyzer clearance (K) associated with the dialysis, and calculating, based at least in part on the length of time, the instantaneous body weight, the volume, and the dialyzer clearance, a urea reduction ratio (URR) associated with the dialysis.

20 Claims, 6 Drawing Sheets

(56) References Cited

U.S. PATENT DOCUMENTS

2008/0076977 A1* 3/2008 Mannheimer et al. ........ 600/301
2012/0330112 A1* 12/2012 Lamego et al. ............... 600/301

FOREIGN PATENT DOCUMENTS

WO WO2011026646 A1 3/2011
WO WO 2011026646 A1 * 3/2011 .............. A61M 1/16

* cited by examiner

DETERMINING DIALYSIS TREATMENT EFFECTIVENESS

TECHNICAL FIELD

This disclosure relates to determining dialysis treatment effectiveness.

BACKGROUND

Dialysis is a treatment used to support a patient with insufficient renal function. One type of dialysis is hemodialysis. During hemodialysis ("HD"), the patient's blood is passed through a dialyzer of a dialysis machine while also passing a dialysis solution or dialysate through the dialyzer. A semipermeable membrane in the dialyzer separates the blood from the dialysate within the dialyzer and allows diffusion and osmosis exchanges to take place between the dialysate and the blood stream. These exchanges across the membrane result in the removal of waste products, including solutes like urea and creatinine, from the blood. These exchanges also regulate the levels of other substances, such as sodium and water, in the blood. In this way, the dialysis machine acts as an artificial kidney for cleansing the blood.

SUMMARY

One aspect of the subject matter described in this specification may be embodied in a method performed on a dialysis machine that includes receiving a first value that represents a pre-dialysis body weight of a patient and receiving a second value that represents a volume of liquid (V) inside a body of the patient. The method also includes administering dialysis to the patient, calculating an instantaneous body weight (W) of the patient based at least in part on the first value, determining a length of time (t) for which the dialysis was administered to the patient, determining a dialyzer clearance (K) associated with the dialysis, and calculating, based at least in part on the length of time, the instantaneous body weight, the volume, and the dialyzer clearance, a urea reduction ratio (URR) associated with the dialysis.

Another aspect of the subject matter described in this specification may be embodied in a dialysis machine that includes one or more processing devices and one or more memory devices. The one or more memory devices include instructions that, when executed by the one or more processing devices, cause the one or more processing devices to perform operations including receiving a first value that represents a pre-dialysis body weight of a patient and receiving a second value that represents a volume of liquid (V) inside a body of the patient. The operations also include administering dialysis to the patient, calculating an instantaneous body weight (W) of the patient based at least in part on the first value, determining a length of time (t) for which the dialysis was administered to the patient, determining a dialyzer clearance (K) associated with the dialysis, and calculating, based at least in part on the length of time, the instantaneous body weight, the volume, and the dialyzer clearance, a urea reduction ratio (URR) associated with the dialysis.

An additional aspect of the subject matter described in this specification may be embodied in one or more computer storage devices storing instructions that, when executed by one or more processing devices, cause the one or more processing devices to perform operations including receiving a first value that represents a pre-dialysis body weight of a patient and receiving a second value that represents a volume of liquid (V) inside a body of the patient. The operations also include administering dialysis to the patient, calculating an instantaneous body weight (W) of the patient based at least in part on the first value, determining a length of time (t) for which the dialysis was administered to the patient, determining a dialyzer clearance (K) associated with the dialysis, and calculating, based at least in part on the length of time, the instantaneous body weight, the volume, and the dialyzer clearance, a urea reduction ratio (URR) associated with the dialysis.

These aspects and other embodiments may each optionally include one or more of the following features.

A graphical representation of the urea reduction ratio is presented on a display associated with the dialysis machine.

An ultrafiltrate value (UF) associated with the dialysis is determined.

Calculating an instantaneous body weight of the patient includes subtracting the ultrafiltrate value from the first value.

Calculating the urea reduction ratio includes iteratively evaluating an algorithm.

Calculating the urea reduction ratio further includes providing an estimated value for the urea reduction ratio.

The algorithm is represented by the expression:

$$URR = URR - \frac{f(URR)}{f'(URR)}$$

F(URR) is evaluated according to the expression:

$$f(URR) = \frac{Kt}{V} + \ln((1 - URR) - 0.008t) - (0.5 + 3.5URR)\left(\frac{UF}{W}\right)$$

Calculating the urea reduction ratio further includes iteratively evaluating the expression $$URR = URR - \frac{f(URR)}{f'(URR)}$$

until a predetermined condition is satisfied.

The predetermined condition is represented by the expression:

$$\left|\frac{f(URR_n)}{f'(URR_n)}\right| > 0.01$$

The expression Kt/V is evaluated to provide a Kt/V value.

A signal is received on the dialysis machine to cause a display of the dialysis machine to toggle between a presentation of the urea reduction ratio and the Kt/V value.

Other embodiments of these aspects include corresponding systems, apparatus, and computer programs, configured to perform the actions of the methods, encoded on computer storage devices.

These and other embodiments may each optionally include one or more of the following features.

These and other embodiments may provide one or more of the following advantages.

A urea reduction ratio (URR) can be automatically determined based on well-established techniques for determining a Kt/V ratio. A user can be allowed to view both Kt/V and URR, for example, on a display associated with a dialysis machine. Reports and bills can be generated that include a URR associated with dialysis treatment for a patient.

The details of one or more embodiments of the subject matter described in this specification are set forth in the accompanying drawings and the description below. Other potential features, aspects, and advantages of the subject matter will become apparent from the description, the drawings, and the claims.

DETAILED DESCRIPTION

An HD Machine

Figure 1:
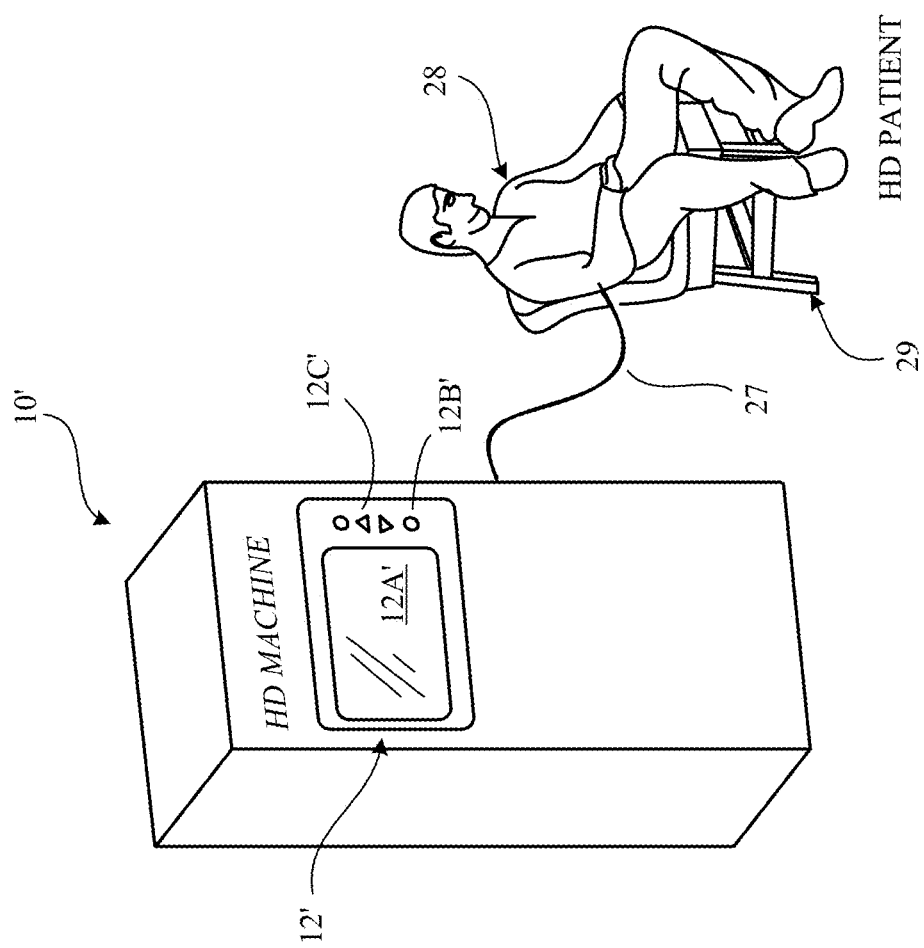
FIG. 1 is a perspective, schematic view of a patient connected to a hemodialysis machine during hemodialysis treatment.

A hemodialysis (HD) machine, is shown in FIG. 1. Hemodialysis is a process which employs a machine that includes a dialyzer to aid patients whose renal function has deteriorated to the point where their body cannot adequately rid itself of toxins. The dialyzer includes a semi-permeable membrane, the membrane serving to divide the dialyzer into two chambers. Blood is pumped through one chamber and a hemodialysis solution through the second. As the blood flows by the dialysis fluid, impurities, such as urea and creatinine, diffuse through the semi-permeable membrane into the hemodialysis solution. The electrolyte concentration of the hemodialysis fluid is set so as to maintain electrolytic balance within the patient.

Further purification in a dialyzer is possible through ultrafiltration. Ultrafiltration results from the normal situation wherein there is a positive pressure differential between the blood and the dialysis fluid chambers. This pressure differential causes water in the blood to pass through the membrane into the hemodialysis solution. This provides the benefit of reducing a hemodialysis patient's excess water load which normally would be eliminated through proper kidney functioning.

Hemodialysis is a complex treatment process in which, typically, an arterio-venous shunt, frequently termed a "fistula," is surgically inserted between a patient's artery and vein to facilitate transfer of blood from the patient to the dialyzer. During a normal hemodialysis treatment, one end of an arterial line or tube is inserted into the upstream end of the fistula (i.e., at a point near the patient's artery) and transports blood withdrawn from the upstream portion of the fistula to the inlet of the dialyzer; a venous line or tube connected to the output of the blood side of the dialyzer returns treated blood to the fistula at an insertion point downstream of the arterial line (i.e., at a point near the patient's vein).

Patients undergoing hemodialysis therapy may travel three or more times per week to hospitals or dialysis treatment centers that are designed for efficient and routine hemodialysis therapy. However, hemodialysis therapy may also be performed at home (as well as, or instead of, at a hospital or dialysis center) under the supervision of a medical assistant or, in some cases, even by the patient undergoing the hemodialysis treatment (i.e., with or without supervision).

FIG. 1 shows an example of a patient care environment that includes an HD machine 10'. The HD machine 10' is configured for use in hemodialysis with a hemodialysis patient (HD patient) 28 seated in a chair 29 so that, e.g., the HD patient 38 may receive hemodialysis treatment from the HD machine 10'. A connector tube or arterial line 27 transports blood from the HD patient 28 to the HD machine 10' and back again to the HD patient 28 after processing and treatment in the HD machine 10'.

The HD machine 10' may include a control panel or display 12', a display screen (e.g., a color LCD touch screen) 12A', arrow keys 12C' and buttons 12B', that together furnish a GUI designed to operated by a user, e.g., the HD patient, or (most often in the case of hemodialysis) a medical assistant or a physician.

As an alternative to a touch screen 12A' and its associated keys 12C' and buttons 12B', the HD machine 10' can include other types of screens and user data entry systems. In certain implementations, for example, the HD machine 10' includes a display screen with buttons (e.g., feathertouch buttons) arranged on the console adjacent the display screen. Certain buttons can be arranged to be aligned with operational options displayed on the screen during use such that the user can select a desired operational option by pressing the button aligned with that operational option. Additional buttons in the form of arrow buttons can also be provided to allow the user to navigate through the various display screens and/or the various items displayed on a particular screen. Other buttons can be in the form of a numerical keypad to allow the user to input numerical values in order, for example, to input operational parameters. A select or enter button can also be provided to allow the user to select an operational option to which the user navigated by using the arrow keys and/or to allow the user to enter values that the user inputted using the numerical keypad.

The HD machine includes one or more processing devices, e.g., a central programmed microprocessor-based controller for directing the hemodialysis treatment according to, e.g., programmed parameters to carry out the HD patient's 28 prescribed hemodialysis treatment. In certain implementations, parameter entries can be made on the control panel 12' of the HD machine 10' for a given therapy mode. During the procedure, information regarding various HD parameters may be recorded by the HD machine 10' and any anomalies or error conditions or alarms generated during the procedure may be noted in the record. In certain implementations, the system is designed to record the date and time, and to create a data record of the HD patient's 28 treatment.

In some examples, successful hemodialysis treatment may include the monitoring of several patient vital signs and hemodialysis parameters during the hemodialysis process in order to optimize the overall efficacy of the hemodialysis procedure, to assess the condition of the fistula (the access to the patient's blood) and to determine the actual purification achieved. In some examples, the efficiency of a dialysis procedure can be monitored and reflected using the ratio Kt/V, where K represents the clearance or dialysance (both terms representing the purification efficiency of the dialyzer), t is treatment time and V is the patient's total water value (e.g., the amount of water in a patient's body, sometimes referred to as the total water volume). The effectiveness of a dialysis treatment can also be represented by another metric: the urea reduction ratio (URR). In some examples, URR is based on measured levels of blood urea before and after treatment, with URR representing the amount of blood urea removed during treatment.

While both Kt/V and URR both represent an effectiveness of a dialysis treatment, there may be instances in which one metric is preferred over the other. For example, Food and Drug Administration (FDA) regulations may require that in order for health care providers to be paid under the Medicare program, bills must be submitted in a format that provides a URR associated with a patient's dialysis treatment.

In some examples, it is possible to provide a URR value associated with a dialysis treatment by determining a Kt/V value and using that Kt/V value to provide a URR value. For example, while a dialysis machine may be configured to measure or receive parameters needed to calculate Kt/V, a process can be implemented (e.g., on a dialysis machine) to convert the Kt/V value to provide a URR that represents the effectiveness of a dialysis treatment. Furthermore, a dialysis machine equipped with such capability can also be configured to provide both a Kt/V value and a URR, and may also include controls for toggling between which metric is used to represent the effectiveness of a dialysis therapy. For example, the dialysis machine 10' may present a representation of the Kt/V value and/or the URR on the touch screen 12A', and may further provide controls that allow a user to select whether none, one, or both of the Kt/V value and the URR are presented on the touch screen 12A'. Examples of these and other techniques are described below with reference to FIGS. 2-7.

Figure 2:
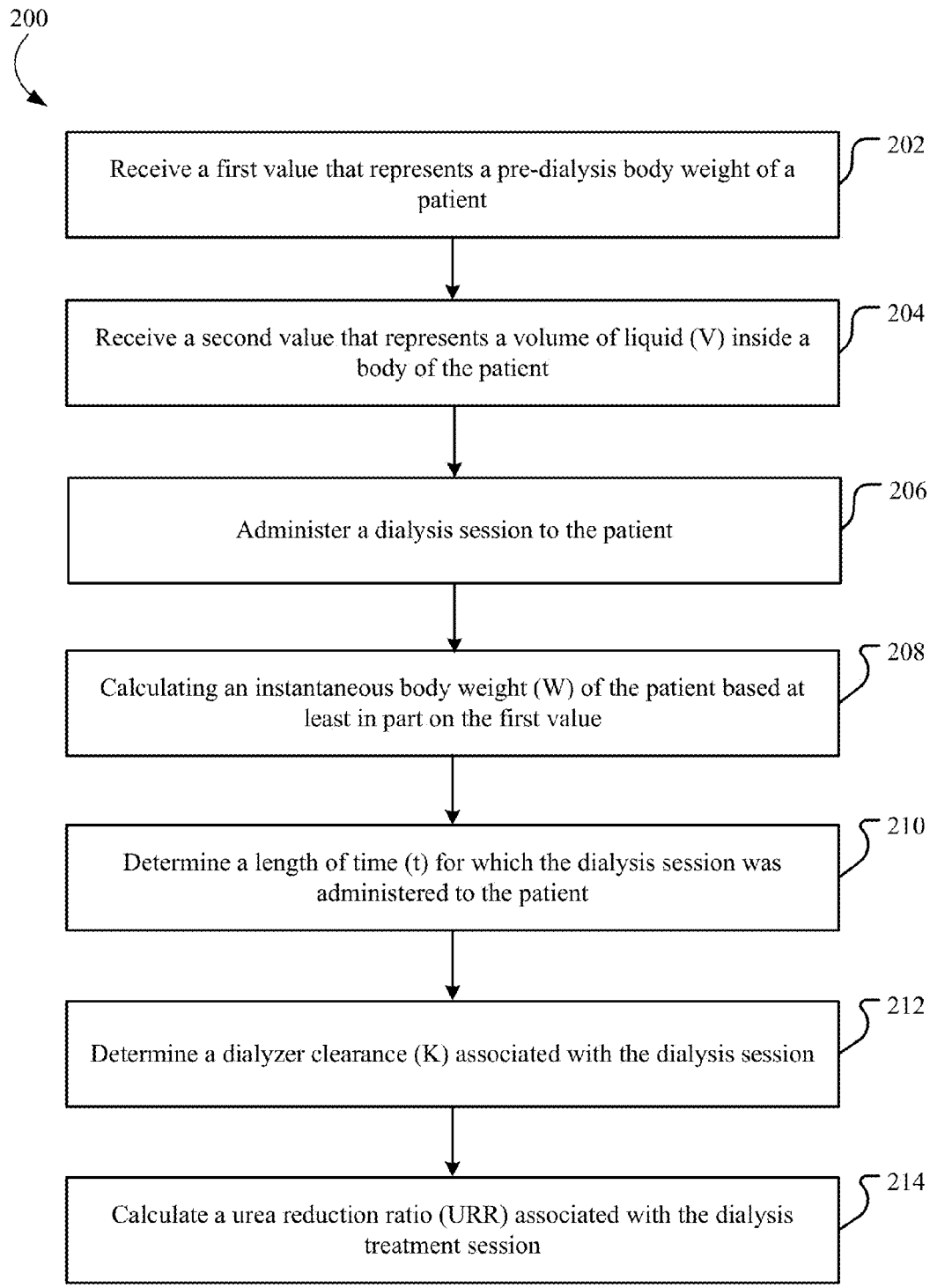
FIG. 2 is a diagram of a process for providing a value that represents an effectiveness of a dialysis treatment.

FIG. 2 illustrates a process 200 for determining a URR associated with a dialysis treatment based on at least some parameters that are associated with the determination of a Kt/V value. A first value is received that represents a pre-dialysis body weight of a patient (202). For example, a user (e.g., a clinician, a physician, or a patient) may enter the patient's body weight into a dialysis machine after weighing the patient on a weigh scale. In some examples, a way scale can be configured to provide a patient's weight directly to a dialysis machine through a wireless or wired communication link (e.g., a Bluetooth®, infrared, WiFi®, or ethernet connection). As an example, a dialysis machine may receive a value of 80 kg that represents the pre-dialysis body weight of a patient.

A second value is received that represents a volume of liquid (V) inside the body of a patient (204). In some examples, the value of V is determined by a physician prior to the dialysis treatment, and may then be entered into the dialysis machine by a user when configuring a dialysis treatment. For example, the value of V can be estimated based on the patient's gender, height, weight, medical history, and physician's observations.

A dialysis is administered to the patient (206). For example, hemodialysis can be administered to the patient using the hemodialysis machine 10'. During the hemodialysis, toxins (e.g., urea) are removed from the patient's body in the manner described above. Administering the dialysis treatment to the patient may also include providing one or more medications to the patient.

An instantaneous body weight (W) of the patient is calculated based at least in part on the first value (208). In some examples, the instantaneous body weight W of a patient refers to a patient's body weight at a specified time (e.g., at a time after the dialysis treatment has commenced). After a dialysis treatment has commenced, a patient's instantaneous body weight W may often differ from a patient's pre-dialysis body weight due to the removal of fluid (e.g., water) from the patient's body during the dialysis treatment. As a result, in order to calculate the instantaneous body weight W of a patient, the calculation compensates for the patient's weight loss during a dialysis treatment. This weight loss factor is referred to as an ultrafiltration (UF) parameter. For example, if the patient's pre-dialysis weight was 80 kg and 2 kg of water was removed from the patient's body during treatment, the patient's ultrafiltration parameter UF would be equal to 2, and the patient's instantaneous body weight W would be equal to 78 kg.

A length of time (t) for which the dialysis was administered to the patient is determined (210). In some examples, the length of time t simply corresponds to a duration of time which has passed between the beginning and the end of a dialysis treatment administered to a patient. However, in some examples, the length of time t may correspond to the beginning of a patient's dialysis treatment and a time other than a time at which the treatment concluded. For example, calculations and determinations associated with the process 200 may be carried out while a patient is undergoing a dialysis treatment and, as such, the time t may represent a time at which a calculation was initiated. The time t can be represented in minutes, hours, or as some other value or denomination of time.

A dialyzer clearance (K) associated with the dialysis is determined (212). In some examples, the dialyzer clearance K can be estimated based on a urea transfer ability of the dialyzer (which, in some cases, may be a function of its size and membrane permeability), a blood flow rate, and a dialysate flow rate. In some dialysis machines, the dialyzer clearance can be estimated by testing an ability of the dialyzer to remove a small salt load added to the dialysate during dialysis. In some examples, a dialyzer clearance K can be measured, estimated, and/or entered into the dialysis machine after at least a portion of dialysis treatment has been performed.

A urea reduction ration (URR) is calculated based at least in part on the length of time t, the instantaneous body weight W, the volume V, and the dialyzer clearance K (214). As described above, it is possible to convert a Kt/V value (or the parameters K, t, and V used in the calculation thereof) into a URR. Some possible techniques are described below.

A dialysis machine may use Kt/V parameters (such as those described above with regard to FIG. 2) in order to calculate a URR. The following formula relates Kt/V with URR:

$$\frac{Kt}{V} = -\ln((1-URR) - 0.008t) + (4 - 3.5(1-URR))\left(\frac{UF}{W}\right)$$

Newton's method may be used to iteratively estimate the value of URR using various derivations of the above expression. In general, Newton's method can be used to find roots of nonlinear equations, such as the expression above, and can evaluate nonlinear equations according to the expression:

$$x_{n+1} = x_n - \frac{f(x_n)}{f'(x_n)}$$

Applying this formula (with n=0) to the initial estimate $x_0$ gives a better estimate $x_1$. This better estimate $x_1$ can then run through the formula again (n=1) in order to provide an even better estimate, $x_2$. This iterative process may be repeated indefinitely to yield a solution to whatever degree of accuracy is desired. A technique for evaluating the accuracy of an estimated value is described in greater detail below.

Thus, solving the formula above for URR (e.g., to provide the function f(URR)) results in the following expression:

$$f(URR) = \frac{Kt}{V} + \ln((1 - URR) - 0.008t) - (0.5 + 3.5URR)\left(\frac{UF}{W}\right)$$

The derivative (f(URR)) of the expression above is represented by the following expression:

$$f'(URR) = \left(\frac{1}{1 - URR - 0.008t}\right) - (3.5)\left(\frac{UF}{W}\right)$$

With f(URR) and f(URR) defined, values for URR can be iteratively approximated using Newton's method and the parameter values K, t, V, W, and UF until a satisfactory URR is provided (e.g., a URR having a value that falls within a predefined threshold).

The following example illustrates a calculation of URR based on a Kt/V value associated with a patient's dialysis treatment. Suppose, for example, that a Kt/V of the dialysis treatment is 1.4, the dialysis treatment time t is 3 hours, the UF parameter is 3 (e.g., 3 liters of water have been removed from the patient) and the patient's instantaneous weight W is 80 kg. To calculate URR, an initial estimate for the value of URR (0.65) is provided. Accordingly, the calculations may resemble the following:

$$f(URR_0) = 1.4 + \ln((1 - 0.65) - 0.008(3)) - (0.5 + 3.5 * 0.65)\left(\frac{3}{80}\right)$$

$$f(URR_0) = 0.16306$$

and $$f'(URR_0) = \left(\frac{1}{1 - 0.65 - 0.008 * 3}\right) - (3.5)(80)$$

$$f'(URR_0) = -3.19873$$

In order to determine whether the value for URR falls within a desired threshold, the following expression can be evaluated:

$$\left|\frac{f(URR_n)}{f'(URR_n)}\right| > 0.01$$

If the above expression is true, the iterative process can continue until |f(URRn)/f'(URRn)|≤0.01. The value of 0.01 is arbitrary, and any value can be used to represent a desired degree of accuracy. Evaluating |f(URRn)/f'(URRn)|>0.01 using the above values results in the following determination:

$$\left|\frac{f(URR_0)}{f'(URR_0)}\right| = \left|\frac{0.16306}{-3.19873}\right| = 0.0541$$

As 0.0541 is not less than 0.01 (the desired accuracy threshold), a new URR value for URR (URR$_1$) is selected based on the previous calculation in order to converge toward a more accurate value for URR. Accordingly, URR1 can be determined according to the following expression:

$$URR_1 = URR_0 - \frac{f(URR_n)}{f'(URR_n)}$$

$$URR_1 = 0.65 - \frac{0.16306}{-3.19873} = 0.7041$$

The numerical value of 0.7041 for URR1 can be used to perform the following calculations:

$$f(URR_1) = 1.4 + \ln((1 - 0.7041) - 0.008(3)) - (0.5 + 3.5 * 0.7041)\frac{3}{80}$$

$$f(URR_1) = -0.01551$$

and $$f'(URR_1) = -\left(\frac{1}{1 - 0.65 - 0.008 * 3}\right) - (3.5 * 3)(80)$$

$$f'(URR_1) = -3.8091$$

To determine whether this value of URR is accurate enough to satisfy the threshold, the same accuracy determination described above is repeated with the newly calculated values f(URR$_1$) and f'(URR$_1$), yielding the following determination:

$$\left|\frac{f(URR_1)}{f'(URR_1)}\right| = \left|\frac{-0.01551}{-3.8091}\right| = 0.00407$$

As 0.00407 is less than the desired accuracy threshold of 0.01, the iterative process for determining a final value of URR can be completed according to the following determination:

$$URR_2 = URR_{final} = URR_1 - \frac{f(URR_1)}{f'(URR_1)}$$

$$URR_{final} = 0.7041 - \frac{-0.01551}{-3.8091} = 0.70003$$

$$URR_{final} = 70\%$$

Figure 4:
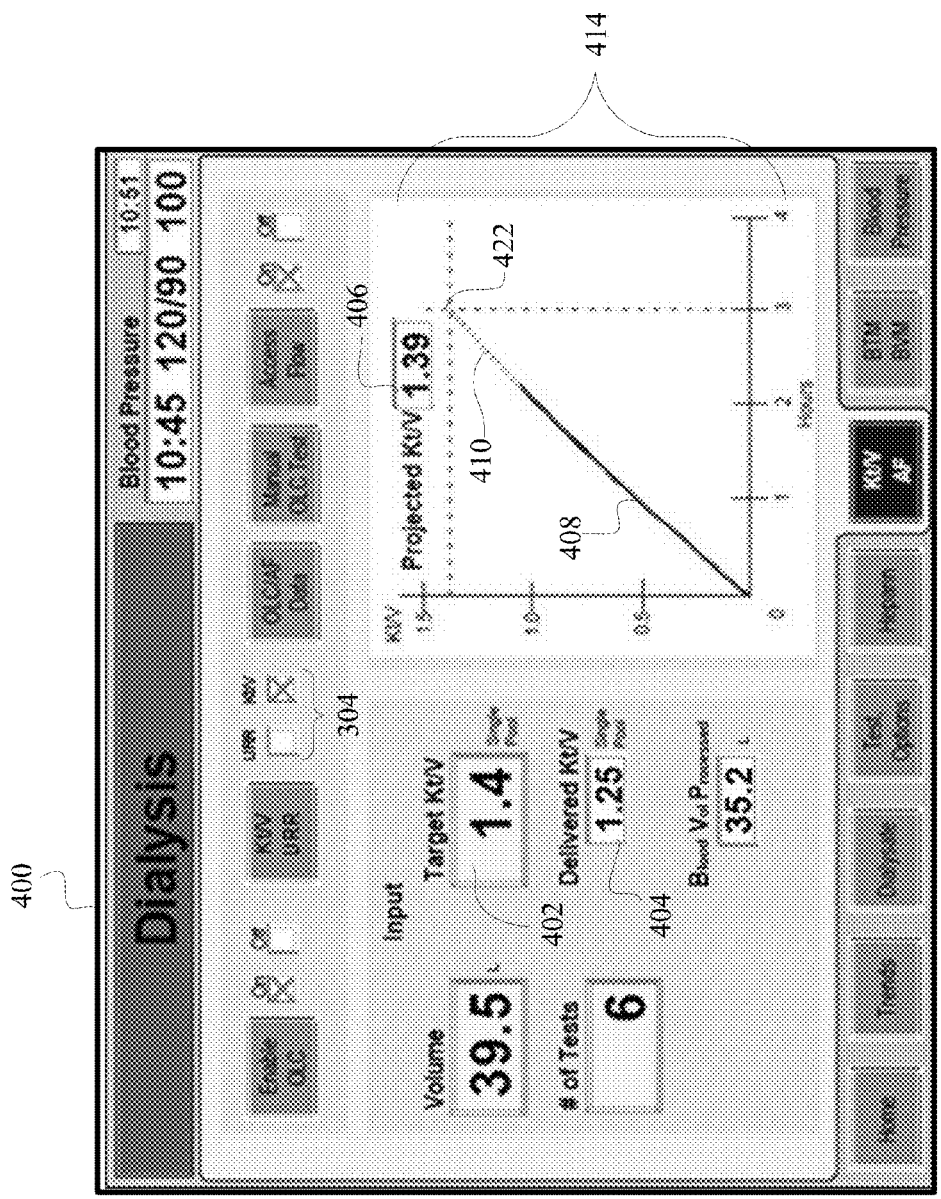
FIG. 4 is a diagram of a user interface associated with the machine of FIG. 1.
Figure 5:
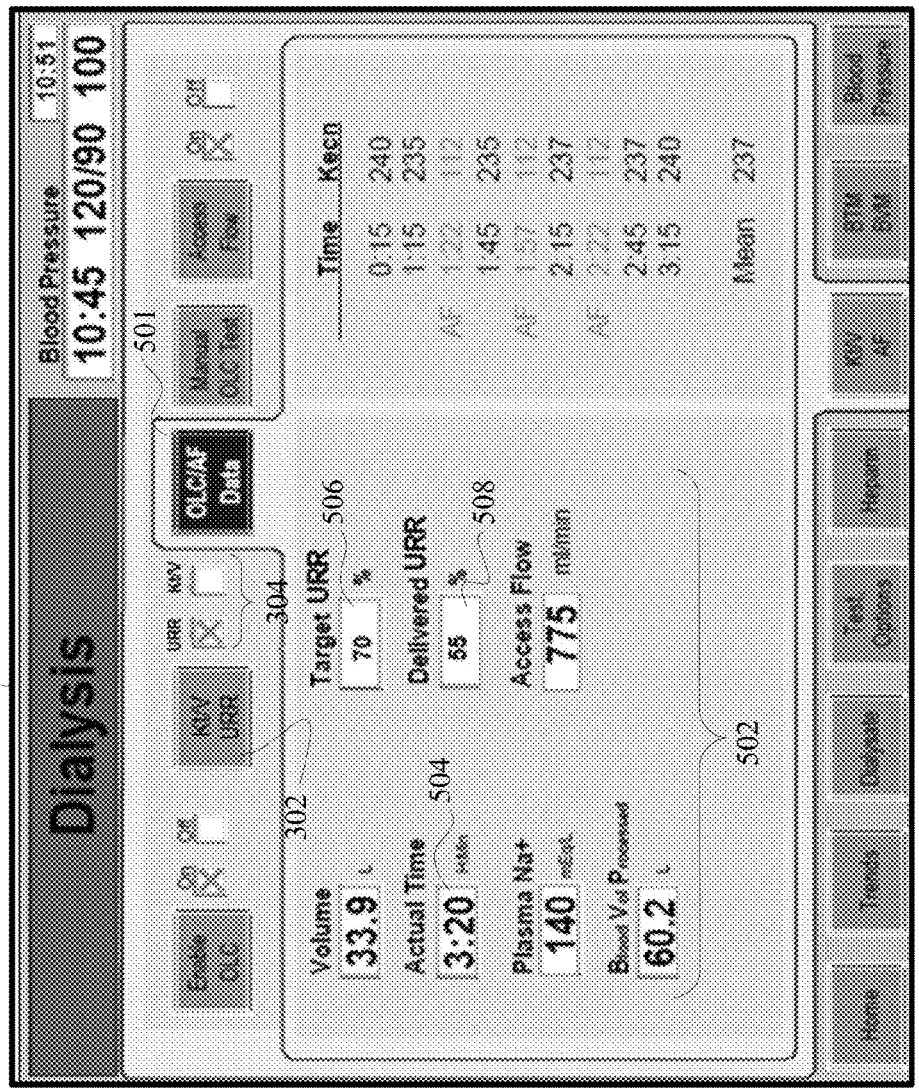
FIG. 5 is a diagram of a user interface associated with the machine of FIG. 1.

Accordingly, in this example, the approximate value of URR for a dialysis treatment with a corresponding Kt/V value of 1.4 would be 70%. Although the calculation took only two iterations in this example, the calculation may continue for any number of iterations based on factors such as the predefined error tolerance and the accuracy of the initial URR value estimate. After the URR has been calculated, the dialysis machine can display the URR on a display associated with the dialysis machine (e.g., a display screen integral to the dialysis machine or a remote display in communication with the dialysis machine), or can store or transmit the URR to another location. For example, the dialysis machine may track the URR over time in order to generate a URR histogram, or may transmit the URR to a location so that a patient's medical record can be updated to include the URR. Some examples of the display and use of the URR are shown in FIGS. 3-5.

Figure 3:
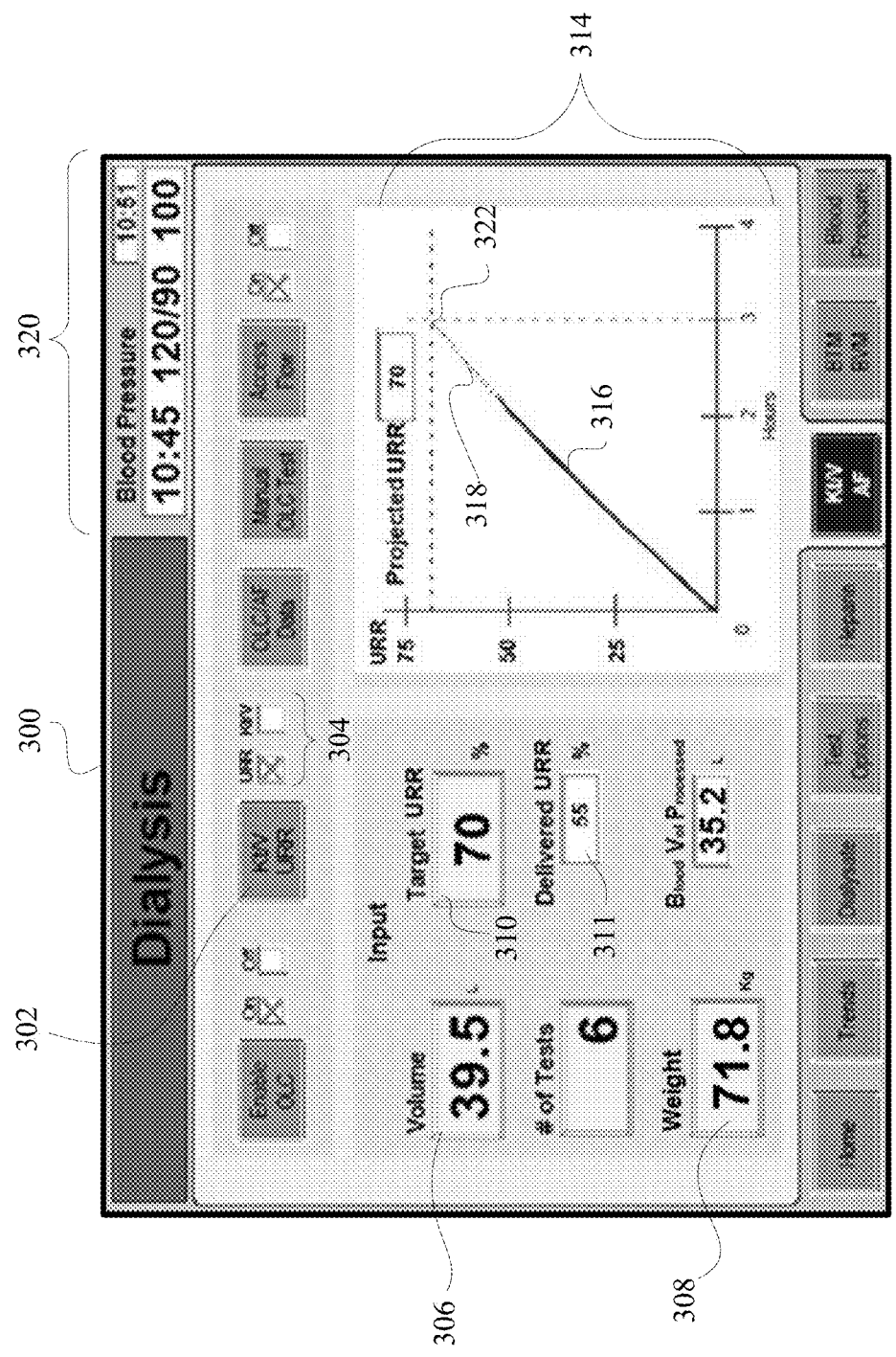
FIG. 3 is a diagram of a user interface associated with the machine of FIG. 1.

FIG. 3 shows a user interface 300 that could be presented on a dialysis machine, such as the HD machine 10' (FIG. 1B). In general, the user interface 300 presents information related to a dialysis treatment of a patient. The user interface 300 presents patient vital information 320 which, in this example, is blood pressure data. The user interface 300 also presents a number of parameters that relate specifically to dialysis. For example, the user interface 300 includes a pre-dialysis weight W of the patient (71.8 kg) and a volume of water in the patient's body (39.5 L).

The user interface 300 also includes a target URR 310, which represents a level of treatment that will be provided to a patient. In this example, the target URR 310 is 70%. The level of treatment provided to a patient can be tracked by a delivered URR 311 which, in this example, is 55%. In some examples, a dialysis treatment can be configured to continue until the delivered URR 311 meets or exceeds the target URR. The delivered URR 311 may be updated in substantially real time, or may be updated periodically or on demand (e.g., in response to user input, or in response to a control signal). In some examples, the delivered URR 311 can be updated in response to a signal that indicates that the amount of treatment provided to a patient has changed by an amount that exceeds a threshold. For example, the delivered URR 311 can be configured to be updated in response to a determination that the delivered URR 311 has increased by 1%.

The user interface 300 includes a graphical display 314 that provides a visual representation of the progress of a dialysis treatment. In this example, the graphical display 314 is a line graph that maps URR versus time. The graphical display 314 includes a first component 316 (a solid line) that corresponds to the level of treatment provided to a patient during a dialysis treatment, and a second component 318 (a dashed line) that corresponds to an expected level of treatment over a future period of time. In this case, the first component 316 and the second component 318 correspond to the delivered URR 311 (55%) and the target URR 310 (70%), respectively. That graphical display 314 may also include a critical point 322 that represents the point in time at which the delivered URR 311 will meet the target URR 310. In this example, the critical point 322 has been estimated as occurring after three hours of dialysis treatment.

The user interface 300 also includes a toggle control 302 that, when activated (e.g., by pressing the toggle control 302 on a touch screen of the dialysis machine), allows a user to toggle between a display of URR values (e.g., target URR 310 and delivered URR 311) and Kt/V values. The user interface 300 may also include radio controls 304 for specifying whether the user interface 300 will display none, one, or both of URR values and Kt/V values. Activation of the toggle control 302 or of the radio controls 304 can cause a dialysis machine to alter the user interface 300, or may cause the dialysis machine to display a new user interface, such as the user interface 400 shown in FIG. 4. In this example, URR values are displayed in the user interface 300, as only the URR option associated with the radio control 304 has been selected.

FIG. 4 shows a user interface 400 that displays information related to a dialysis treatment for a patient after the user has activated the toggle button 302 to cause various parameters related to Kt/V to be displayed. In some examples, the user interface 400 may be presented, for example, on a display associated with the dialysis machine. Unlike the user interface 300, the user interface 400 displays dialysis related information in the Kt/V format, which may result from the activation of the toggle control 302. The interface 400 presents parameters in the Kt/V format that relate to a dialysis treatment. For example, the user interface 400 includes a target Kt/V 402 and a delivered Kt/V 404. As in the user interface 300, the user interface 400 also includes a graphical display 414 that provides a visual representation of the progress of a dialysis treatment. In this example, the graphical display 414 is a line graph that maps Kt/V (y-axis) versus time (x-axis). The graphical display 414 includes a first component 408 (a solid line) that corresponds to the level of treatment provided to a patient during a dialysis treatment, and a second component 410 (a dashed line) that corresponds to an expected level of treatment over a future period of time. In this case, the first component 408 and the second component 410 correspond to the delivered Kt/V 404 (1.25) and the target Kt/V 402 (1.4), respectively. That graphical display 414 may also include a critical point 422 that represents the point in time at which the delivered Kt/V 404 will meet the target Kt/V 402. In this example, the critical point 422 has been estimated as occurring after three hours of dialysis treatment.

FIG. 5 shows a user interface 500 that also displays information related to a dialysis treatment after the user has activated a OLC/AF tab control 501 to display various parameters associated with dialysis treatment. More specifically, the user interface 500 displays information about blood volume processed and access flow. The user interface 500 also displays the K values of the OLC tests and the time. More specifically, the user interface 500 includes treatment parameters 502, such as a treatment time 504, a target URR 506, and a delivered URR 508. In some examples, the treatment time 504 can correspond to a length of time (t) for which the dialysis treatment was administered to a patient. Like the user interface 300 and the user interface 400, the user interface 500 includes the toggle control 302 and the radio control 304 for selecting whether to display Kt/V values and/or URR values.

The systems, software, methods, and techniques described herein can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired, and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files, such devices include magnetic disks, such as internal hard disks and removable disks magneto-optical disks and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

Figure 6:
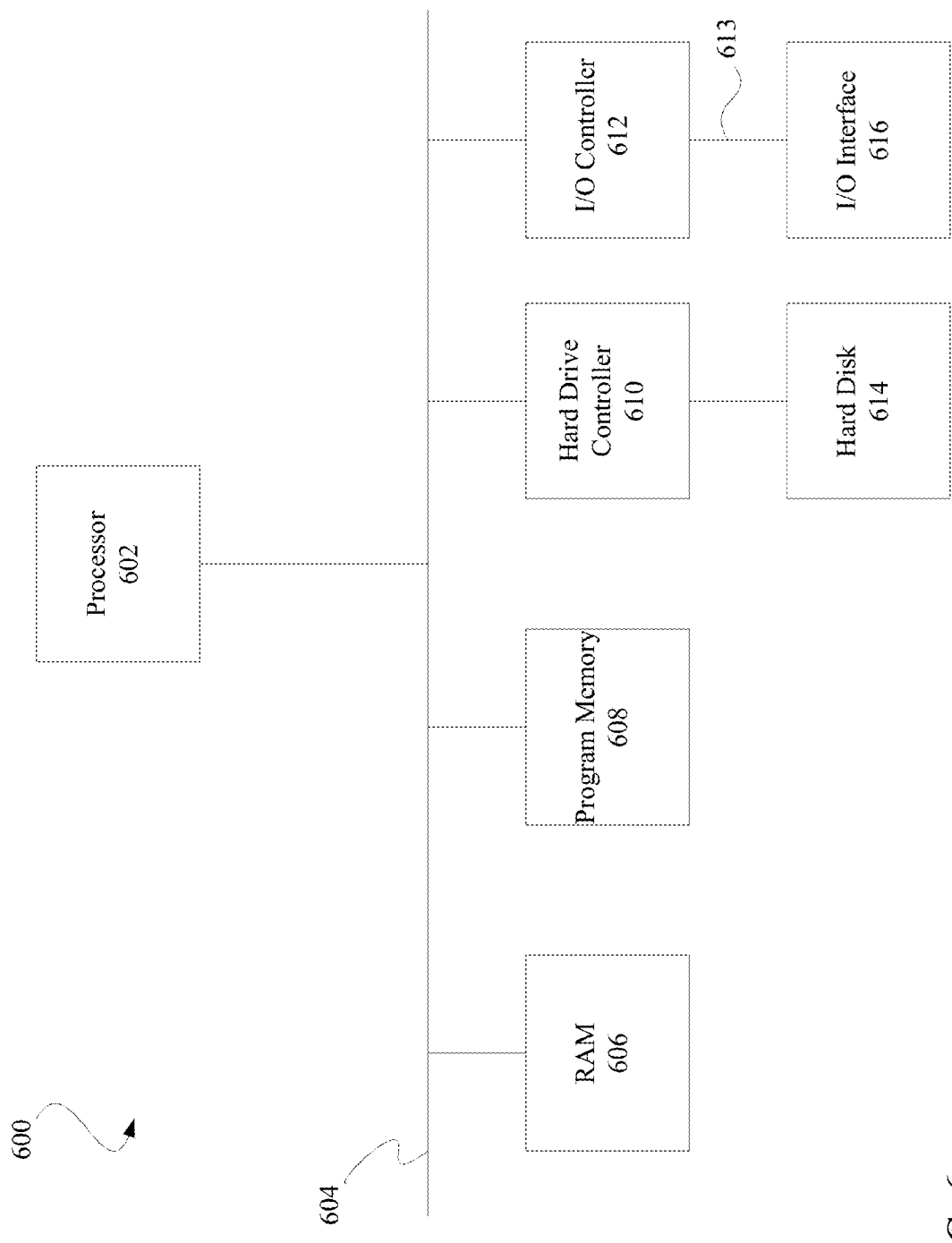
FIG. 6 is a diagram of a computing system.

FIG. 6, which shows a block diagram of a possible programmable processing system 600 that can be provided in the HD machine 10' for implementing and/or performing the apparatus or methods described herein. The system 600 includes a processor 602, a random access memory (RAM) 606, a program memory 608 (for example, a writeable read-only memory (ROM) such as a flash ROM), a hard drive controller 610, and an input/output (I/O) controller 612 coupled by a processor (CPU) bus 604. The system 600 can be preprogrammed, in ROM, for example, or it can be programmed (and reprogrammed) by loading a program from another source (for example, from a floppy disk, a CD-ROM, or another computer).

The hard drive controller 610 is coupled to a hard disk 614 suitable for storing executable computer programs, including programs embodying the present techniques. The I/O controller 612 is coupled by an I/O bus 613 to an I/O interface 616. The I/O interface 616 receives and transmits data in analog or digital form over communication links such as a serial link, local area network, wireless link, and parallel link. In some examples, the I/O interface 616 can include a software and/or a hardware interface to facilitate communication between the system 600 and an I/O device of a dialysis machine, or may be or comprise one or more I/O devices of a dialysis machine (e.g., a touchscreen, such as the touchscreen 12A'.

While displays of an HD machine have been described as displaying the various Kt/V and URR parameters, other displays can alternatively or additionally be used.

What is claimed is:

1. A method comprising:
   providing a hemodialysis machine comprising tubes to transfer blood between a patient and the machine, a display screen, and one or more controllers operable for:
   receiving a first value that represents a pre-dialysis body weight of a patient;
   receiving a second value that represents a volume of liquid (V) inside a body of the patient;
   administering a dialysis treatment to the patient;
   while the dialysis treatment is being administered to the patient:
     calculating an instantaneous body weight (W) of the patient based at least in part on the first value;
     determining a length of time (t) for which the dialysis treatment was administered to the patient;
     determining a dialyzer clearance (K) associated with the dialysis treatment;
   calculating, based at least in part on the length of time, the instantaneous body weight, the volume of liquid, and the dialyzer clearance, a urea reduction ratio (URR) associated with the dialysis treatment;
   providing a user interface for display on the display screen of the hemodialysis machine comprising:
     a set of controls that enable a user to control whether or not either of a URR value and a Kt/V value are presented on the display, and enabling the user to toggle between presentation of a Kt/V value and presentation of a URR value on the display, comprising a toggle control to enable toggling between a display of a URR value and a Kt/V value, and radio controls specifying whether the user interface displays one or both of Kt/V values and URR values,
     providing, for display on the display screen of the hemodialysis machine, a visual representation of the progress of the dialysis treatment that includes at least one graph having an x-axis and a y-axis,
     wherein the x-axis represents a time value, and the y-axis represents at least one of the Kt/V value and the URR value,
     wherein the y-axis represents the Kt/V value if a Kt/V option is chosen on the controls, and the y-axis represents URR if the URR option is chosen on the controls, and
     wherein the graph includes at least one component representing either of the correlation of time to Kt/V and the correlation of time to URR; and
   continuing administration of dialysis until a delivered URR value tracked by the user interface meets or exceeds a target URR value.

2. The method of claim 1, wherein the one or more controllers are further operable for presenting a graphical representation of the urea reduction ratio on the display associated with the dialysis machine.

3. The method of claim 1, wherein the one or more controllers are further operable for determining an ultrafiltrate value (UF) associated with the dialysis treatment.

4. The method of claim 3, wherein calculating an instantaneous body weight of the patient comprises subtracting the ultrafiltrate value from the first value.

5. The method of claim 1, wherein calculating the urea reduction ratio comprises iteratively evaluating an algorithm.

6. The method of claim 5, wherein calculating the urea reduction ratio further comprises providing an estimated value for the urea reduction ratio.

7. The method of claim 5, wherein the algorithm is represented by the expression:

$$URR = URR - f(URR)/f'(URR)$$

wherein f(URR) is a function for determining URR, and f'(URR) is a function for determining the derivative of URR.

8. The method of claim 7, wherein the one or more controllers are further operable for evaluating f(URR) according to the expression:

$$K*t/V + \ln((1-URR) - 0.008*t) - (0.5 + 3.5*URR)*0.55*UF/W.$$

9. The method of claim 7, wherein calculating the urea reduction ratio further comprises iteratively evaluating the expression URR=URR−f(URR)/ f'(URR) until a predetermined condition is satisfied, wherein f(URR) is a function for determining URR, and f'(URR) is a function for determining the derivative of URR.

10. The method of claim 9, wherein the predetermined condition is represented by the expression:

$$|f(URR)/f'(URR)| < 0.01.$$

11. The method of claim 1, wherein the one or more controllers are further operable for evaluating Kt/V to provide a Kt/V value.

12. The method of claim 1, wherein the component of the graph comprises a line.

13. The method of claim 1, wherein the graph includes a first component that corresponds to the level of treatment provided to the patient during the dialysis treatment, and a second component that corresponds to an expected level of treatment over a future period of time.

14. The method of claim 1, wherein the graph indicates a critical point that represents a point in time at which either or both of a delivered Kt/V value will meet a target Kt/V value and a delivered URR will meet a target URR value.

15. A hemodialysis machine comprising:
   tubes to transfer blood between a patient and the machine;
   a display screen;
   one or more processing devices; and
   one or more memory devices comprising instructions that, when executed by the one or more processing devices, cause the one or more processing devices to perform operations comprising:
     receiving a first value that represents a pre-dialysis body weight of a patient;
     receiving a second value that represents a volume of liquid (V) inside a body of the patient;
     causing a dialysis treatment to be administered to the patient;

while the dialysis treatment is being administered to the patient:
calculating an instantaneous body weight (W) of the patient based at least in part on the first value;
determining a length of time (t) for which the dialysis treatment was administered to the patient;
determining a dialyzer clearance (K) associated with the dialysis treatment;
calculating, based at least in part on the length of time, the instantaneous body weight, the volume of liquid, and the dialyzer clearance, a urea reduction ratio (URR) associated with the dialysis treatment;
providing a user interface for display on the display screen of the hemodialysis machine comprising:
a set of controls that enable a user to control whether or not either of a URR value and a Kt/V value are presented on the display and enabling the user to toggle between presentation of a Kt/V value and presentation of a URR value on the display, the set of controls comprising a toggle control to enable toggling between a display of a URR value and a Kt/V value, and radio controls specifying whether the user interface displays one or both of Kt/V values and URR values,
providing, for display on the display screen of the hemodialysis machine, a visual representation of the progress of the dialysis treatment that includes at least one graph having an x-axis and a y-axis,
wherein the x-axis represents a time value, and the y-axis represents at least one of the Kt/V value and the URR value,
wherein the y-axis represents the Kt/V value if a Kt/V option is chosen on the controls, and the y-axis represents URR if the URR option is chosen on the controls, and
wherein the graph includes at least one component representing either of the correlation of time to Kt/V and the correlation of time to URR; and
continuing administration of dialysis until a delivered URR value tracked by the user interface meets or exceeds a target URR value.

16. The hemodialysis machine of claim 15, wherein calculating the urea reduction ratio comprises iteratively evaluating an algorithm.

17. The hemodialysis machine of claim 15, wherein calculating the urea reduction ratio further comprises providing an estimated value for the urea reduction ratio.

18. The hemodialysis machine of claim 15, wherein the component of the graph comprises a line.

19. The hemodialysis machine of claim 15, wherein the graph includes a first component that corresponds to the level of treatment provided to the patient during the dialysis treatment, and a second component that corresponds to an expected level of treatment over a future period of time.

20. The hemodialysis machine of claim 15, wherein the graph indicates a critical point that represents a point in time at which either or both of a delivered Kt/V value will meet a target Kt/V value and a delivered URR will meet a target URR value.

* * * * *

UNITED STATES PATENT AND TRADEMARK OFFICE
CERTIFICATE OF CORRECTION

PATENT NO. : 9,155,823 B2
APPLICATION NO. : 13/214519
DATED : October 13, 2015
INVENTOR(S) : Jeffrey Tarn, Fei Wang and Aiyuan Wang Page 1 of 1

It is certified that error appears in the above-identified patent and that said Letters Patent is hereby corrected as shown below:

Claims

At Column 12, line 21, in Claim 7, delete "f(URR)" and insert --f'(URR)--.

Signed and Sealed this
Eighth Day of March, 2016

Michelle K. Lee
*Director of the United States Patent and Trademark Office*